(12) United States Patent
Zhang et al.

(10) Patent No.: US 11,772,499 B2
(45) Date of Patent: Oct. 3, 2023

(54) METHOD AND DEVICE FOR CONTROL OF A MOBILITY DEVICE

(71) Applicant: Shift Robotics, Inc., Austin, TX (US)

(72) Inventors: Xunjie Zhang, Pittsburgh, PA (US); Anand Kapadia, Annandale, VA (US)

(73) Assignee: Shift Robotics, Inc., Austin, TX (US)

( * ) Notice: Subject to any disclaimer, the term of this patent is extended or adjusted under 35 U.S.C. 154(b) by 0 days.

(21) Appl. No.: 17/843,153

(22) Filed: Jun. 17, 2022

(65) Prior Publication Data

US 2022/0314103 A1    Oct. 6, 2022

Related U.S. Application Data

(63) Continuation of application No. 16/629,252, filed as application No. PCT/US2018/041345 on Jul. 9, 2018, now Pat. No. 11,364,431.

(60) Provisional application No. 62/530,177, filed on Jul. 8, 2017.

(51) Int. Cl.
| | |
|---|---|
| *A63C 17/12* | (2006.01) |
| *B60L 15/20* | (2006.01) |
| *B60L 15/38* | (2006.01) |
| *B60W 40/08* | (2012.01) |
| *B60W 50/08* | (2020.01) |
| *A61B 5/11* | (2006.01) |
| *B60W 50/00* | (2006.01) |

(52) U.S. Cl.
CPC ........... *B60L 15/2009* (2013.01); *B60L 15/38* (2013.01); *B60W 40/08* (2013.01); *B60W 50/082* (2013.01); *A61B 5/112* (2013.01); *A63C 17/12* (2013.01); *A63C 2203/12* (2013.01); *A63C 2203/18* (2013.01); *A63C 2203/24* (2013.01); *B60L 2200/24* (2013.01); *B60L 2240/42* (2013.01); *B60W 2050/0014* (2013.01); *B60W 2050/0064* (2013.01)

(58) Field of Classification Search
CPC ..................................................... A63C 17/12
See application file for complete search history.

(56) References Cited

U.S. PATENT DOCUMENTS

| | | |
|---|---|---|
| 833,100 A | 10/1906 | Wells |
| 1,672,700 A | 6/1928 | Vass |
| 1,801,205 A | 4/1931 | Mirick |
| 2,857,008 A | 10/1958 | Pirrello |
| 3,392,986 A | 7/1968 | Ryan |

(Continued)

FOREIGN PATENT DOCUMENTS

| | | |
|---|---|---|
| CN | 2759524 Y | 2/2006 |
| CN | 201423154 Y | 3/2010 |

(Continued)

OTHER PUBLICATIONS

European Supplementary Search Report for EP 18831335.7 dated Feb. 3, 2021.

(Continued)

*Primary Examiner* — Erez Gu Rari
(74) *Attorney, Agent, or Firm* — DLA Piper LLP (US)

(57) ABSTRACT

A system for control of a mobility device comprising a controller for analyzing data from at least one sensor on the mobility device, wherein the data is used to determine the gait of user. The gait data is then used to provide motion command to an electric motor on the mobility device.

13 Claims, 3 Drawing Sheets

(56) References Cited

U.S. PATENT DOCUMENTS

| | | |
|---|---|---|
| 4,334,690 A | 6/1982 | Klamer et al. |
| 4,417,737 A | 11/1983 | Suroff |
| 4,553,767 A | 11/1985 | Robjent et al. |
| RE32,346 E | 2/1987 | Klamer et al. |
| 4,932,676 A | 6/1990 | Klamer |
| 5,056,802 A | 10/1991 | Piotrowski |
| 5,236,058 A | 8/1993 | Yamet et al. |
| 5,400,484 A | 3/1995 | Gay |
| 5,413,380 A | 5/1995 | Fernandez |
| 5,730,241 A | 3/1998 | Shyr et al. |
| 5,797,466 A | 8/1998 | Gendle |
| 6,059,062 A * | 5/2000 | Staelin ............... B60L 3/0092 180/181 |
| 6,322,088 B1 | 11/2001 | Klamer et al. |
| 6,425,587 B1 | 7/2002 | Moon |
| 6,497,421 B1 | 12/2002 | Edgerley et al. |
| 6,517,091 B1 | 2/2003 | Fisher et al. |
| 6,645,126 B1 | 11/2003 | Martin et al. |
| 7,163,210 B1 | 1/2007 | Rehkemper et al. |
| 7,204,330 B1 | 4/2007 | Lauren |
| 9,027,690 B2 | 5/2015 | Chavand |
| 9,295,302 B1 | 3/2016 | Reed et al. |
| 9,925,453 B1 | 3/2018 | Tuli |
| 10,456,698 B2 | 10/2019 | Chen et al. |
| 10,709,961 B2 | 7/2020 | Zhang et al. |
| 10,933,298 B2 | 3/2021 | Zhang et al. |
| 10,933,299 B2 | 3/2021 | Zhang et al. |
| 11,364,431 B2 | 6/2022 | Zhang et al. |
| 2001/0022433 A1 | 9/2001 | Chang |
| 2003/0047893 A1 | 3/2003 | Pahis |
| 2003/0141124 A1 | 7/2003 | Mullet |
| 2004/0239056 A1 | 12/2004 | Cho et al. |
| 2005/0046139 A1 | 3/2005 | Guan |
| 2005/0082099 A1 | 4/2005 | Tuli |
| 2006/0027409 A1 | 2/2006 | Adams et al. |
| 2007/0090613 A1 | 4/2007 | Lyden |
| 2007/0273110 A1 | 11/2007 | Brunner |
| 2008/0093144 A1 | 4/2008 | Manor |
| 2009/0120705 A1 | 5/2009 | McKinzie |
| 2010/0207348 A1 | 8/2010 | Othman |
| 2012/0285756 A1 | 11/2012 | Treadway |
| 2013/0025955 A1 | 1/2013 | Chavand |
| 2013/0123665 A1 | 5/2013 | Mariani et al. |
| 2013/0226048 A1 | 8/2013 | Unluhisarcikli et al. |
| 2013/0274640 A1 | 10/2013 | Butters et al. |
| 2013/0282216 A1 | 10/2013 | Edney |
| 2014/0196757 A1 | 7/2014 | Goffer |
| 2015/0196403 A1 | 7/2015 | Kim et al. |
| 2015/0196831 A1 | 7/2015 | Treadway et al. |
| 2015/0352430 A1 | 12/2015 | Treadway et al. |
| 2016/0045385 A1 | 2/2016 | Aguirre-Ollinger et al. |
| 2016/0058326 A1 | 3/2016 | Winfree et al. |
| 2016/0113831 A1 | 4/2016 | Hollander |
| 2016/0250094 A1 | 9/2016 | Amundson et al. |
| 2016/0331557 A1 | 11/2016 | Tong et al. |
| 2017/0055880 A1 | 3/2017 | Agrawal et al. |
| 2017/0181917 A1 | 6/2017 | Ohta et al. |
| 2017/0182397 A1 | 6/2017 | Zhang |
| 2017/0259162 A1 | 9/2017 | Mo |
| 2017/0259811 A1 | 9/2017 | Coulter et al. |
| 2017/0296116 A1 | 10/2017 | McCarthy et al. |
| 2018/0008881 A1 | 1/2018 | Mo |
| 2018/0015355 A1 | 1/2018 | Desberg et al. |
| 2018/0333080 A1 | 11/2018 | Malawey et al. |
| 2019/0061557 A1 | 2/2019 | Quick et al. |
| 2019/0184265 A1 | 6/2019 | Micacchi |
| 2019/0314710 A1 | 10/2019 | Zhang et al. |
| 2019/0351315 A1 | 11/2019 | Li |
| 2020/0000373 A1 | 1/2020 | Agrawal et al. |
| 2020/0061444 A1 | 2/2020 | Zhang et al. |
| 2020/0061445 A1 | 2/2020 | Zhang et al. |
| 2020/0129843 A1 | 4/2020 | Zhang et al. |
| 2020/0129844 A1 | 4/2020 | Zhang et al. |
| 2020/0197786 A1 | 6/2020 | Artemev |
| 2021/0015200 A1 | 1/2021 | Tuli |
| 2021/0113914 A1 | 4/2021 | Zhang |

FOREIGN PATENT DOCUMENTS

| | | |
|---|---|---|
| CN | 201565096 U | 9/2010 |
| CN | 101912680 A | 12/2010 |
| CN | 101912681 A | 12/2010 |
| CN | 102167117 A | 8/2011 |
| CN | 102805928 A | 12/2012 |
| CN | 203389316 U | 1/2014 |
| CN | 104689559 A | 6/2015 |
| CN | 204364838 U | 6/2015 |
| CN | 204395401 U | 6/2015 |
| CN | 105214299 A | 1/2016 |
| CN | 106039689 A | 10/2016 |
| CN | 205627021 U | 10/2016 |
| CN | 106390428 A | 2/2017 |
| CN | 106390430 A | 2/2017 |
| CN | 106582003 A | 4/2017 |
| EP | 0686412 A2 | 12/1995 |
| EP | 0834337 A2 | 4/1998 |
| EP | 0894515 A1 | 2/1999 |
| EP | 3629925 A1 | 4/2020 |
| GB | 2452563 A | 3/2009 |
| JP | 2005081038 A | 3/2005 |
| JP | 2013111118 A | 6/2013 |
| WO | 2011092443 A2 | 8/2011 |
| WO | 2018082192 A1 | 5/2018 |
| WO | 2018082193 A1 | 5/2018 |
| WO | 2018082194 A1 | 5/2018 |
| WO | 2018082195 A1 | 5/2018 |
| WO | 2019014152 A1 | 1/2019 |
| WO | 2019014154 A1 | 1/2019 |
| WO | 2019212995 A1 | 11/2019 |
| WO | 2020146680 A1 | 7/2020 |

OTHER PUBLICATIONS

International Search Report and Written Opinion for PCT/CN2017/000499 dated Oct. 20, 2017.
International Search Report and Written Opinion for PCT/CN2017/000500 dated Oct. 20, 2017.
International Search Report and Written Opinion for PCT/CN2017/000501 dated Nov. 3, 2017.
International Search Report and Written Opinion for PCT/CN2017/000502 dated Oct. 13, 2017.
International Search Report and Written Opinion for PCT/US2018/041343 dated Sep. 7, 2018.
International Search Report and Written Opinion for PCT/US2018/041345 dated Sep. 7, 2018.
International Search Report and Written Opinion for PCT/US2019/029742 dated Aug. 26, 2019.
International Search Report and Written Opinion for PCT/US2020/012992 dated Apr. 1, 2020.
International Search Report and Written Opinion for PCT/US2021/056014 dated Jan. 18, 2022.

* cited by examiner

METHOD AND DEVICE FOR CONTROL OF A MOBILITY DEVICE

CROSS-REFERENCE TO RELATED APPLICATIONS

This application is a continuation of U.S. patent application Ser. No. 16/629,252, filed Jan. 7, 2020, which is the U.S. national phase under 35 U.S.C. § 371 of International Application No. PCT/US2018/041345, filed Jul. 9, 2018, which claims the benefit under 35 U.S.C. § 119 of U.S. Provisional Application No. 62/530,177, filed Jul. 8, 2017, each of which is incorporated herein by reference in its entirety.

STATEMENT REGARDING FEDERALLY SPONSORED RESEARCH

Not applicable.

BACKGROUND OF THE INVENTION

The invention relates to a mobility device. More specifically, the invention relates to a control system and method of controlling a mobility device having an electric motor that is worn on the feet of a user to provide mobility assistance.

Commuters and other travelers often have to walk the final leg of their trip, regardless of whether they travelled by car, bus, train, or other means. Depending on the distance, the time needed to complete this final leg of the journey can comprise a significant amount of the total duration of the trip. While bikes or scooters can be used, they are bulky and require skill and a minimum level of fitness to operate. Powered systems, such as moving walkways, suffer from a lack of mobility. Other mobility solutions suffer the same drawbacks or lack the ability to adapt to a particular user. Therefore, it would be advantageous to develop a control system for a mobility device that does not require any special skills or user training and can adapt to the individual needs of a particular user.\

BRIEF SUMMARY

According to embodiments of the present invention is system and method of controlling a pair of mobility device, wherein the mobility devices are worn on each foot of a user. A sensor in each mobility device obtains data about the gait of a user and transmits the data to a processor. The processor analyzes the gait of a user and then uses the gait data to develop motion commands for each mobility device. Each mobility device may comprise a motor, gearing, and wheels. When worn on the feet of a user, the mobility devices allow a user to walk at an increased rate of speed for a given cadence and stride length, as compared to their speed without the mobility devices. Further, the control system adapts to a user so no learning or other control inputs are required by the user.

DETAILED DESCRIPTION

Figure 1:
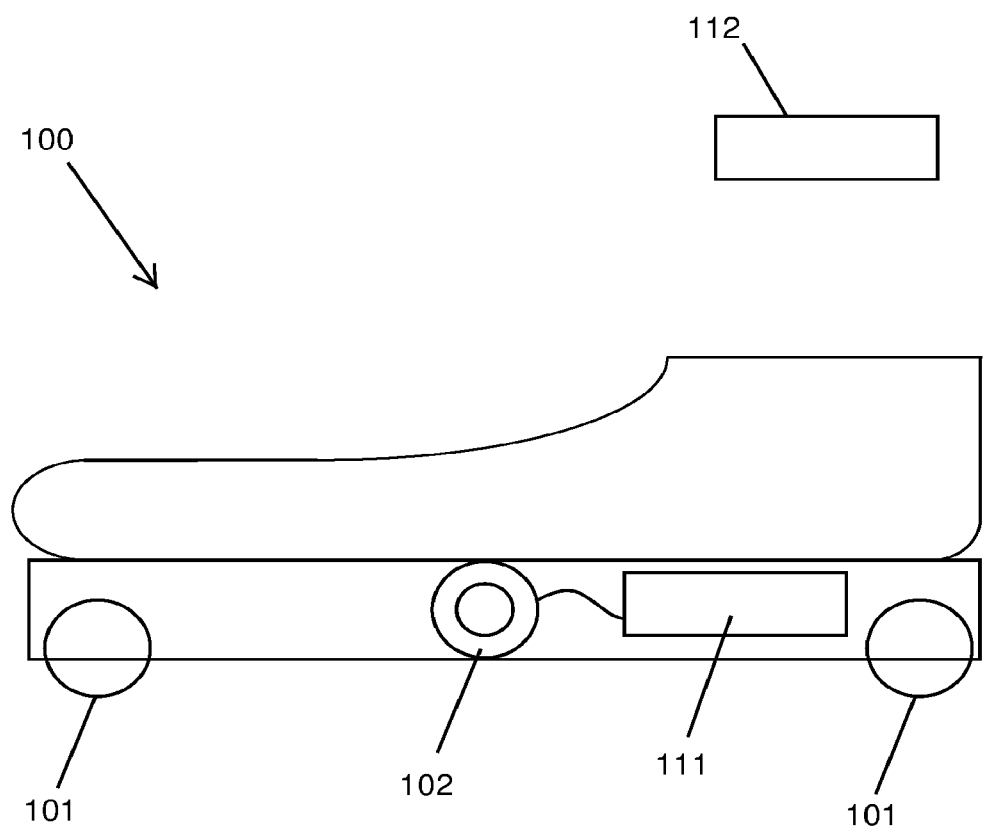
FIG. 1 depicts a mobility device with an embedded controller, according to one embodiment.

As shown in FIG. 1, a mobility device 100, according to one embodiment, comprises a plurality of wheels 101, with at least one of the wheels 101 connected to an electric motor 102. Further shown in FIG. 1 is an onboard controller 111 and an optional remote controller 112. During typical use, a user will wear two mobility devices 100, one on each foot. The mobility device 100 enables a pedestrian to walk faster than a normal walking pace by adding torque to the wheels 101 of the mobility device 100 worn on the foot in contact with the ground. In this manner, the user experiences an effect similar to that of walking on a moving walkway. More specifically, the control system 110 of the present invention enables a user to maintain a normal walking motion by adapting the control of the motor 102 to the movements of the user. As will be discussed in greater detail, the speed at which the wheels 101 spin, through a torque applied by the motor 102, is controlled in part by an analysis of the user's gait.

Figure 2:
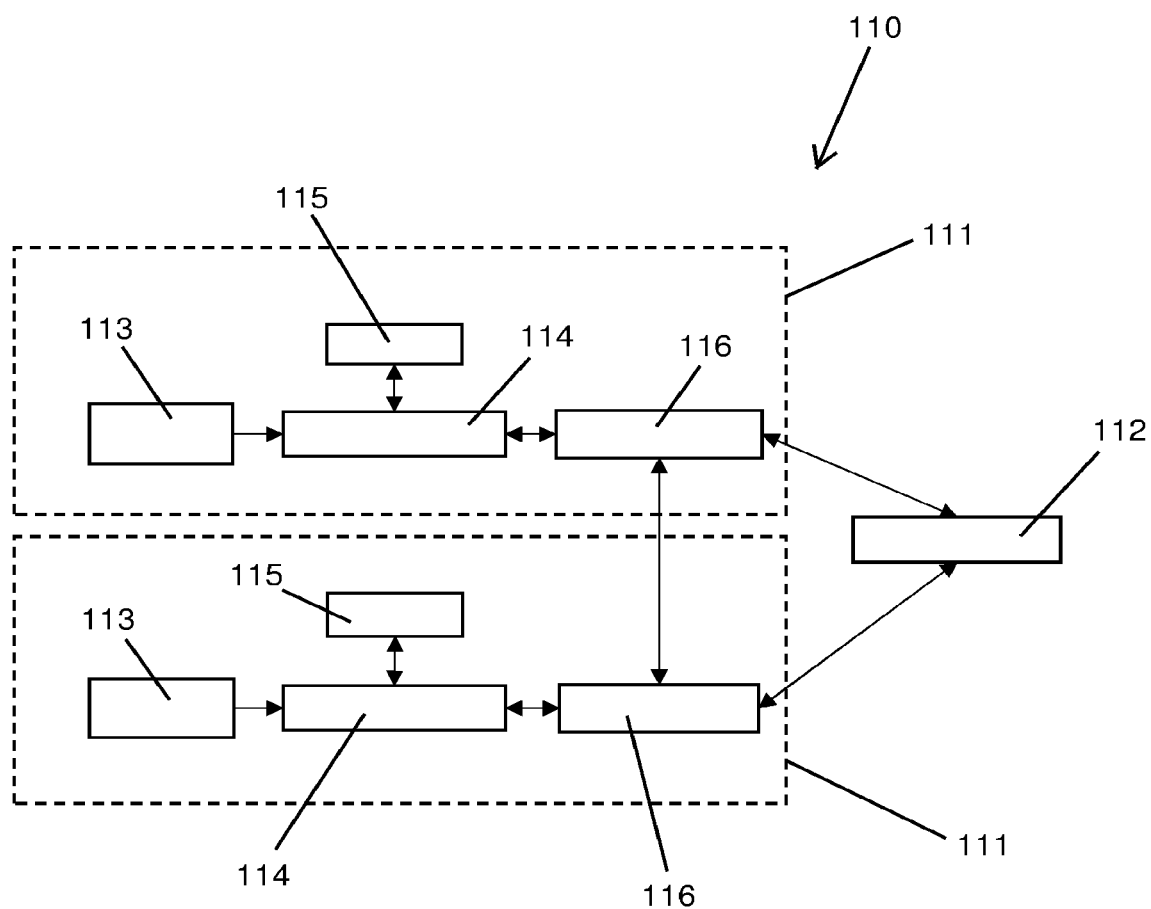
FIG. 2 is a block diagram of a control system according to one embodiment.

FIG. 2 depicts the components of the onboard controller 111, which comprises at least one inertial measurement unit 113, a processor 114, a motor driver 115, and a wireless communication module 116. Two onboard controllers 111 are shown in FIG. 2 since each mobility device (i.e. one for each foot of the user) will house an onboard controller 111. In an alternative embodiment, the control system 110 may also include a remote controller 112, which is capable of sending commands to each of the onboard controllers 111. In this particular embodiment, both the left and right mobility devices 100 receive command speeds from the remote controller 112, which can be in the form of a hand-held controller, a computer, or a mobile phone, and actuate the mobility devices at the specified command speeds.

The control system 110 is used to collect data and analyze the gait of a user. When a pair of mobility devices 100 is worn by a user, each mobility device 100 will have a control system 110. For example, the onboard processor 114 reads gait dynamic data, which may comprise acceleration, angular rates, orientation, gyroscopic data, or quaternion data of each mobility device 100 from the inertial measurement unit 113. In one embodiment, both onboard controllers 111 send the gait dynamic data to the remote controller 112 and, in return, receive a motion command from the remote controller 112. The motion command comprises, for example, acceleration to a set speed, braking, deceleration to a set speed, and holding at a constant speed. In alternative embodiments, additional data can be included in the motion command. Upon receiving the motion command, the onboard processer 114 along with the motor driver 115 converts the motion command into a motor driving signal and drives the motor system 102, thereby affecting the speed of the wheels 101. In one embodiment, the motor driver 115 receives a speed command and drives the motor 102 at the command speed via a feedback loop control.

Figure 3:
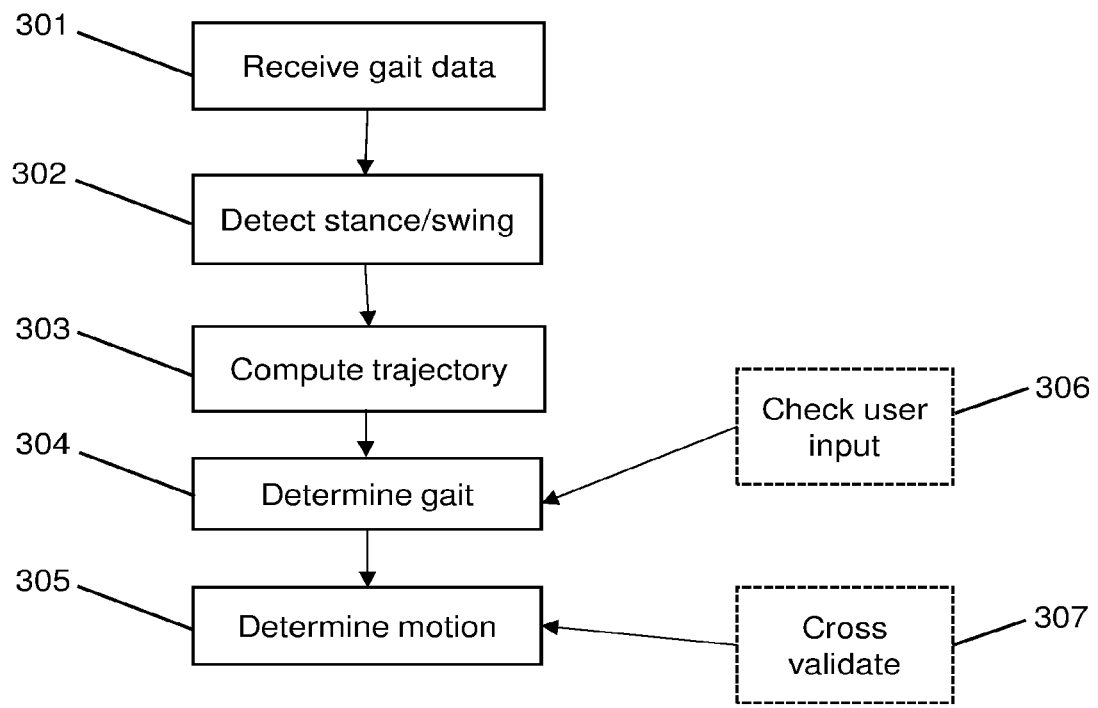
FIG. 3 shows the steps of the method of control, utilizing the controller depicted in FIG. 2.

The flow diagram shown in FIG. 3 depicts the method of gait-based motion control, according to one embodiment, comprising the steps of receiving gait dynamic data 301, detecting the stance/swing phase 302, computing the gait trajectory vector 303, determining the user gait 304, and determining the motion command 305.

In step 301, the control system 110 receives gait dynamic data from both onboard controllers 111. The gait dynamic data includes data collected from the inertial measurement unit 113 in each mobility device 100. Next, in step 302, the control system 110 determines the status of each mobility device 100 as being 'in stance' (i.e. on the ground) or 'swing' (i.e. in the air). Then, in step 303, if the mobility device 100 is in the stance phase, a gait trajectory vector is set to zero. The gait trajectory vector may comprise an estimated foot velocity, stride length, orientation, and elevation, among other parameters. For example, acceleration in the x direction can be integrated over a period of time to determine forward velocity. Similarly, acceleration in the z direction can be used to derive elevation. By way of further example, if the elevation is positive, this could indicate that a user is climbing stairs. A negative elevation can indicate a user is travelling down a set of stairs. Acceleration in the y direction (i.e. side-to-side) can be used to derive orientation, which may be indicative of a turning motion by the user. If the mobility device 100 is in swing phase, a gait speed and trajectory vector are calculated based on the gait dynamic data. For example, in one embodiment, the acceleration data acquired from the inertial measurement units 113 is integrated to provide a velocity for each mobility device 100. The average of the velocity of both mobility devices 100 can be used to calculate the user's overall speed.

Next, at step 304, the gait speed and trajectory vectors are compared against a pre-configured gait model (or profile) which comprises a range of speeds during walking, different ranges of elevation during walking, climbing hills, or stepping on stairs. Based on the result of said comparisons, the user gait is determined. Once gait is determined, at step 305 the motion command is generated based on the determined gait. For example, if the average velocity of the two mobility devices 100 is calculated to be 1.2 m/s, then the gait is determined to be 'middle' (or any other assigned profile based on the average velocity) and requires a motion command for a wheel speed of 0.8 m/s. A lower average velocity may require a motion command with a lower wheel speed.

However, in optional step 306, the remote controller 112 checks if any user input has been registered. The user input can be in various forms such as pressing a button or moving the remote controller 112 in a certain trajectory. For example, the user input may press a button indicating that the user wants forward motion. Thus, the forward motion command received from the user can override the motion command provided by the controller 112 or onboard processors 111. After checking for a user input at step 306, a motion command is generated and sent by the remote controller 112 to both onboard controllers 111. However, if the user input is received from step 306, the final motion command is replaced with the user input before being sent to the onboard controllers 111.

In an alternative embodiment, each onboard controller 111 determines the gait in step 304 and generates a motion command in step 305. To prevent inconsistent commands from each onboard controller 111, each sends the motion command signal to the other for cross-validation in step 307. The motion command may include acceleration to a set speed, braking, deceleration to a set speed, and holding at a constant speed. Upon validating the motion command, the processor 114 along with the motor driver 115 convert the motion command into a motor driving signal and drive the motor system. Stated differently, in step 307, cross validation compares the motion commands generated by each of the two mobility devices 100. For example, the motor driver 115 will only command motor speed when both commands are similar and will brake when the speed commands are inconsistent.

While the disclosure has been described in detail and with reference to specific embodiments thereof, it will be apparent to one skilled in the art that various changes and modification can be made therein without departing from the spirit and scope of the embodiments. Thus, it is intended that the present disclosure cover the modifications and variations of this disclosure provided they come within the scope of the appended claims and their equivalents.

What is claimed is:

1. A mobility device comprising:
a motor;
at least one inertial measurement unit; and
a controller configured to:
receive gait dynamic data from the at least one inertial measurement unit, wherein the gait dynamic data comprises gyroscopic data,
determine a gait of a user based on the gait dynamic data, and
generate a motion command based on the gait.

2. The mobility device of claim 1, wherein the gait dynamic data further comprises at least one of acceleration data, angular rate data, orientation data, or quaternion data.

3. The mobility device of claim 1, wherein the controller is further configured to detect a stance/swing phase of the mobility device based on the gait dynamic data.

4. The mobility device of claim 1, wherein the controller is further configured to compute a gait trajectory vector, wherein the gait trajectory vector comprises a foot velocity.

5. The mobility device of claim 4, wherein the gait trajectory vector further comprises a stride length of the user.

6. The mobility device of claim 4, wherein the gait trajectory vector further comprises an orientation of the mobility device.

7. The mobility device of claim 4, wherein the gait trajectory vector further comprises an elevation of the mobility device.

8. The mobility device of claim 1, further comprising a remote control configured to override the motion command based on a user input.

9. The mobility device of claim 8, wherein the remote control is a mobile phone.

10. The mobility device of claim 1, wherein the controller is further configured to compare the gait of the user against a pre-configured gait model.

11. The mobility device of claim 10, wherein the pre-configured gait model comprises a range of velocities for walking on various inclines.

12. The mobility device of claim 10, wherein the pre-configured gait model comprises a range of velocities for walking on stairs.

13. A method of controlling a mobility device comprising:
receiving gait dynamic data from at least one inertial measurement unit of the mobility device, wherein the gait dynamic data comprises gyroscopic data;
determining a gait of a user based on the gait dynamic data;
generating a motion command for the mobility device based on the gait.

* * * * *